(12) United States Patent
Hutter et al.

(10) Patent No.: US 7,826,993 B2
(45) Date of Patent: **\*Nov. 2, 2010**

(54) METHOD AND DEVICE FOR ANALYZING SUBSTANCES

(75) Inventors: Thomas Hutter, Niederrohrdorf (CH); Christoph Heitz, Elgg (CH); Jurgen Schawe, Bichelsee (CH)

(73) Assignee: Mettler-Toledo AG, Greifensee (CH)

( \* ) Notice: Subject to any disclaimer, the term of this patent is extended or adjusted under 35 U.S.C. 154(b) by 161 days.

This patent is subject to a terminal disclaimer.

(21) Appl. No.: 11/813,332

(22) PCT Filed: Jan. 4, 2005

(86) PCT No.: PCT/EP2005/000027

§ 371 (c)(1),
(2), (4) Date: Dec. 14, 2007

(87) PCT Pub. No.: WO2006/072261

PCT Pub. Date: Jul. 13, 2006

(65) Prior Publication Data

US 2008/0208546 A1    Aug. 28, 2008

(51) Int. Cl.
*G01D 3/00* (2006.01)
(52) U.S. Cl. ............ 702/108; 374/10; 374/43; 702/85; 702/127
(58) Field of Classification Search ............ 702/85, 702/108, 109, 127, 130; 374/10, 14, 46; 73/596
See application file for complete search history.

(56) References Cited

U.S. PATENT DOCUMENTS 3,946,598 A   3/1976   Towne
5,346,306 A *  9/1994   Reading et al. ............ 374/10
5,788,373 A    8/1998   Huetter
6,170,984 B1   1/2001   Schawe
6,336,741 B1   1/2002   Blaine
7,470,058 B2 * 12/2008   Hutter et al. ................. 374/43

FOREIGN PATENT DOCUMENTS

EP    0559362 A1    9/1993
EP    1091208 A1    4/2001
EP    1371324 A1    12/2003

OTHER PUBLICATIONS

Rolf Isermann; Identifikation dynamischer Systeme; Article; 1988; 17 pages; Springer-Verlag, Berlin, Heidelberg, New York, London, Paris, Tokyo 1988.

\* cited by examiner

*Primary Examiner*—John H Le
(74) *Attorney, Agent, or Firm*—Schwabe, Williamson & Wyatt, P.C.

(57) ABSTRACT

Some of the embodiments of the present disclosure provide a method for analyzing a substance, where the method includes subjecting the substance to a dynamic excitation to produce an observable response, and determining a characteristic quantity of the substance based on a correlation between the excitation and the response. The correlation between the excitation and the response is expressed by a parametric model for which a specific model structure with a finite number of unspecified parameters is preset. The determining a characteristic quantity of the substance includes calculating the parameters of the model from values of the excitation and the response in a time domain, determining from the calculated parameters a transfer function in a frequency range, and calculating the characteristic quantity directly from the transfer function. Other embodiments are also described and claimed.

36 Claims, 2 Drawing Sheets

METHOD AND DEVICE FOR ANALYZING SUBSTANCES

CROSS REFERENCE TO RELATED APPLICATIONS

The present application is a national phase entry of, and claims priority under 35 U.S.C. §120 to International Patent Application No. PCT/EP2005/000027, filed Jan. 4, 2005, entitled "Method and Device for Analyzing Substances" and which designates the United States of America, the entire content and disclosure of which is hereby incorporated by reference in its entirety.

TECHNICAL FIELD

The present invention relates to methods for analyzing substances, in which a substance is subjected to a dynamic excitation which causes an observable response, and in which a characteristic quantity of the substance is determined from the correlation between the excitation and the response. The present invention further relates to devices for implementing the methods.

BACKGROUND

The evaluation of a response of a substance to an excitation acting upon the substance enables the determination of characteristic quantities of the substance corresponding to substance properties and substance parameters in the analysis interval covered by the observation. The substance subjected to the excitation may be a pure substance as well as a system or mixture of substances or materials. A widely known example of such a method is dynamic thermal analysis, in which the excitation is effected via a predetermined temporal temperature program to which the substance is subjected and in which the heat flow produced by the sample is captured as a response. Often, this process is implemented as a differential method in which the substance and a known reference substance are excited in accordance with the temperature program and the difference between the heat flows produced by the substance and the reference substance is used as the response. Another well-known example is the thermo-mechanical analysis, in which the response is observed in terms of a change in length of the body of a sample substance, as a function of a predetermined temperature program.

For a known differential thermal analytical method (Euro. Pat. Pub. No. EP 0 559 362 A1), the temperature program implementing the excitation consists of a ramp ascending in a linear manner, which is superimposed by a periodic temperature modulation of preset frequency and preset amplitude. The evaluation of the modulated heat flow difference obtained as the response is based on the split of the response signal representing this heat flow difference into two signal components. One of the signal components is obtained by averaging over one or several modulation periods, respectively, i.e., it constitutes a common component contained in the response signal. The other signal component is the alternating component contained in the response signal, with said alternating component oscillating with the preset modulation frequency and being established by determining the difference between the measured response signal and its common component. This type of excitation and evaluation of the response signal is based on the use of a single preset modulation frequency, with only such events being selectively excited which belong to the same frequency or its harmonic waves.

This restriction to a single excitation frequency is avoided by a different generally known thermal analytical method (Euro. Pat. Pub. No. EP 1 091 208 A1), which provides for a stochastic excitation and subjects the response signal to a correlative analysis during its evaluation. However, the required measuring time is increased in the correlative analysis when a high degree of accuracy is needed.

DETAILED DESCRIPTION OF EMBODIMENTS OF THE INVENTION

Figure 1:
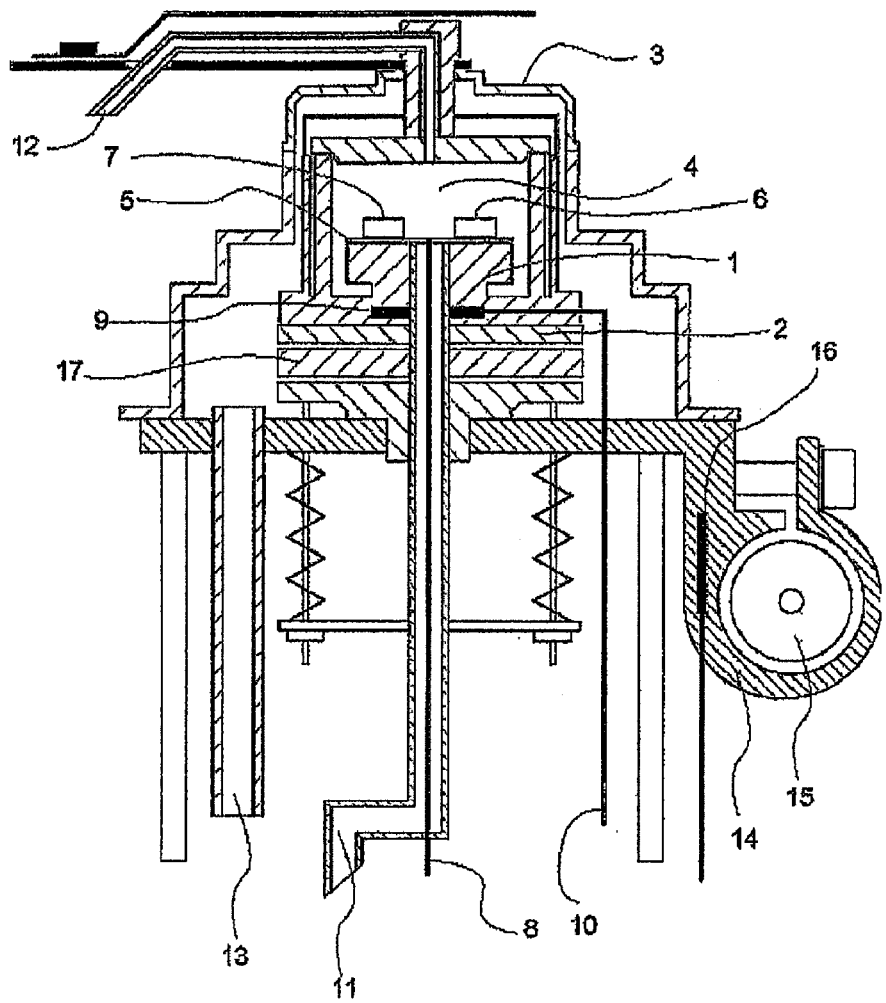
FIG. 1 is a schematic of an difference calorimeter for the implementation of an embodiment of the method in accordance with the present invention.

In light of the foregoing technical problems, embodiments of the present invention are directed to methods for enabling effective evaluation for largely any arbitrary excitation, and also to devices for implementing the methods.

In accordance with the present invention, the foregoing problems are solved, with respect to the methods, in that the correlation between the excitation and the response is expressed by a parametric model, for which a specific model structure with a finite number of unspecified parameters is preset, in that the parameters of the model are calculated from values of the excitation and the associated measured values of the responses in the time domain, in that the transfer function in the frequency range is directly determined from the parameters thus calculated, and in that the characteristic quantity is directly calculated from the transfer function.

Following the calculation of the transfer function performed in accordance with the present invention, the characteristic quantity or the characteristic quantities calculated therefrom reflect the characteristic properties of the substance with a high degree of accuracy. In this context, the excitation, specifically its temporal progression and the corresponding frequency spectrum, may be freely selected and thus adapted so as to favor the discovery of specific properties of the substance. The values of the response are determined via measurement. The values of the excitation may be known or may also be determined via measurement. In the event that the excitation is produced in a device designed for the implementation of the methods in the absence of the substance to be analyzed, the model allows the determination of the characteristic quantities of this device instead of the characteristic quantities of the substance.

An especially important embodiment includes the model being considered as time-invariant and linear. This embodiment of the present invention takes into account the fact that, in many cases, the relation between the excitation and the response is at least approximately linear and time-invariant. In such a linear, time-invariant model, the relation between the input signal corresponding to the excitation and the output signal corresponding to the response may be represented, as is generally known, in the form of a differential equation whose coefficients are the model parameters. In the time-discrete case, a time series of excitation values at equal time intervals and the corresponding measured values of the response are used to determine the parameters of the model, with the time interval being determined by the sampling interval. In this case, as it is generally known, the differential equation of the time-continuous case is approximated by the respective difference equations, and the better the approximation, the smaller the sampling interval or the higher the sampling rate.

This difference equation has the following form:

$$y_k = -a_1 \cdot y_{k-1} - a_2 \cdot y_{k-2} - \ldots - a_{na} \cdot y_{k-na} + b_1 \cdot u_{k-1} + b_2 \cdot u_{k-2} + \ldots + b_{nb} \cdot u_{k-nb} + \varepsilon_k \quad (1)$$

In equation (1), the indices k, k–1, ... designate the discrete values of the sampling times $y_k$, and $u_k$ designates the values of the response or the excitation at these sampling times; $a_1$, $a_2$, ..., $1_{na}$ designate the coefficients of the response values, and $b_1$, $b_2$, ..., $b_{nb}$ designate the coefficients of the excitation values. In equation (1), it was assumed, without restricting its universality, that $a_0=1$. It was also assumed that the coefficient $b_0$ is zero, because this is usually the case in actual systems since an instantaneous effect of the excitation on the response does not occur in practice. But it is pointed out that a non-zero value for $b_0$ could be included in equation (1) above, without this having any effect on the treatment described in the following. And finally, an error term $\varepsilon_k$ was added on the right side of equation (1). It takes into account the variation which occurs between the model and the actual measured process.

If one combines the values of excitation and response, occurring in equation (1), as a value vector $\phi_k$ as per $$\phi_k = [-y_{k-1}, -y_{k-2}, \ldots -y_{k-na}, u_{k-1}, u_{k-2}, \ldots, u_{k-nb}] \quad (2)$$

and the parameter values to be determined as parameter vector $\Theta$ as per $$\Theta = [a_1, a_2, \ldots a_{na}, b_1, b_2, \ldots, b_{nb}]^T \quad (3)$$

then equation (1) takes the following form in matrix notation:

$$y_k = \phi_k \cdot \Theta + \varepsilon_k \quad (4)$$

Hence, for the complete determination of the parameter vector $\Theta$, $n_a+n_b$ equations are required, which requires a sufficient time series of sampling times k, k–1, ..., k–n, i.e., a sufficiently long measurement window. The system of equations is resolved such that the equation error $\varepsilon_k$ is minimized. This can be done, e.g., by using the method of least squares.

In the event that the methods are to be applied to systems in which the correlation between the excitation signal and the response signal contains a non-linear portion which may not or should not be neglected, a first alternative allows deducting all portions of the excitation and/or the response that are not associated with the non-linearity and subjecting only the thus obtained difference signals to the evaluation using the linear time-invariant model. This assumes, however, that the non-linear portions are known or can be determined in some way.

A second alternative, on the other hand, provides for an extension of the time-invariant linear model by adding a mathematical term designed to take into account the non-linear portion in the response. The determinants of this mathematical term can be determined in conjunction with the model parameters from the excitation and the response in the time domain. The response $y_s(t)$ in this case is represented in the form of $$y_s(t) = X(t) + y(t) \quad (5)$$

with y(t) being the linear portion and X(t) being the non-linear portion.

This second alternative is particularly useful for the frequently occurring situations in which the non-linear portion X(t) of the response $y_s(t)$ is only slowly variable as compared to its linear portion y(t). This is the case, for example, in the dynamic thermal analysis, where the heat flow corresponding to the response is composed of a reversible heat flow following the excitation corresponding to rapid changes in the heat rate, with this heat flow being associated with the thermal capacity of the substance, and a non-reversible heat flow which is determined by the thermal properties of the substance (for example phase transformations or chemical reactions). Since thermal events usually take a certain time, the associated heat flow cannot follow rapid changes in the excitation and is variable at a relatively slow rate. That is why, in such cases, the duration of the measurement window required for the calculation of the model parameters is so short relative to the change in the non-linear portion X(t), such that the latter manifests as a constant, i.e., that it can be set, in the respective time window, to be:

$$X = c \quad (6)$$

Given a significant change within the time window, a linear approach can be chosen instead:

$$X(t) = c_0 + c_1 \cdot (t - t_0) \quad (7)$$

wherein $t_0$ designates a freely selectable constant. Advantageously, $t_0$ will be selected to be the time which is in the center of the respective time window used. In the event that this linear approach is not sufficient in terms of the required degree of accuracy either, it is possible to include square terms or higher order terms or other functions in an analogous manner in the ansatz of X(t). In this way, both the linear or reversible portion and the non-linear or non-reversible portion of the response signal are determined separately within the framework of the evaluation.

When a non-linear portion is added in this way, a respective term is added on the right side of equation (1). This means that the parameter vector $\Theta$ is to be extended by respective parameters which are also calculated in the solution of the equation system. Analogously, the vector $\phi_k$ is to be extended.

Under the assumption that, for example, equation (7) is used, the following apply:

$$\phi_k = [1, t, -y_{k-1}, -y_{k-2}, \ldots -y_{k-na}, u_{k-1}, u_{k-2}, \ldots, u_{k-nb}] \quad (8)$$

and $$\Theta = [\gamma_1, \gamma_2, a_1, a_2, \ldots a_{na}, b_1, b_2, \ldots, b_{nb}]^T$$

wherein:

$$\gamma_1 = c_0 \cdot (1 + a_1 + \ldots + a_{na}) - c_1 \cdot (a_1 + 2a_2 + \ldots + pa_{na}) \quad (9)$$

$$\gamma_2 = c_1 \cdot (1 + a_1 + \ldots + a_{na}) \quad (10)$$

Then, equation (4) applies again, wherein the vector $\gamma_k$ is composed of the measured values of $y_s(t)$ in equation (5).

The ansatz, specified in equation (1), for the description of the time-discrete linear time-invariant system can be expressed, as is generally known, using the z transformation in the form of $$y(z) = H(z)u(z) \quad (11)$$

wherein y(z) and u(z) are the z transformed values of the response y(t) or the excitation u(t) and H(z) is the z transformed value of the transfer function. Here, as it is generally known, the variable z is defined as $$z = e^{T_0 s} \quad (11a)$$

wherein $T_0$ is the time interval between the sampling times, i.e., the sampling interval, and the imaginary portion of the variable s corresponds to the frequency ω. In the following, the time unit $T_0=1$, without restriction of generality.

Here, H(z) takes the form $$H(z) = \frac{B(z)}{A(z)} \quad (12)$$

wherein B(z) and A(z) are polynomials, whose degree is $n_b$ or $n_a$, of the variable z with the coefficients $b_1, \ldots, b_{nb}$ or $a_1, \ldots, a_{na}$ from equation (1). It has been shown that this rational expression for H(z) describes many practical cases exactly or in sufficiently acceptable approximation. Thus, equation (11) can be written in the form of $$A(z)y(z) = B(z)u(z) \quad (13)$$

In this representation, it can also be applied to multiple quantity systems in which the excitation consists of more than one input signal and/or the response consists of more than one response signal. A(z) then is a matrix which contains the coefficients of the associated denominator polynomial for each output signal of the response. B(z) is a matrix which contains the coefficients of the associated numerator polynomial for each input signal of the excitation. Persons skilled in the art will not encounter any particular problems in trying to apply the specified equations to multiple quantity systems. Information on this subject can be found in textbooks, for example in the MatLab User Manual: System Identification Toolbox User's Guide; The MathWork, Inc.—Nov. 2000, 4 printing for version 5.0 (Release 12), pages 3-37-3-39. The above explanation of the procedural principle based on the example involving an input signal u(t) of the excitation and an output signal y(t) or $y_s(t)$ of the response should therefore not be understood in a restrictive sense. Instead, the method also includes excitations having more than one excitation signal and/or responses having more than one response signal.

Advantageously, for the determination of the model structure within the framework of the present invention, the number $n_a$ of coefficients of the response values $y_1$ and the number $n_b$ of coefficients of the excitation values $u_m$ are preset in the difference equation. These numbers may be varied in order to optimize the model structure until an optimum match of the correlation, described by the model, between the excitation and the response and the measured values is achieved.

An especially important application of the present invention is found in the known area of dynamic thermal analytical techniques. Here, the excitation signal often consists of the overlay of a constant heat rate $\beta_u$ with a periodically and non-periodically variable portion $u_t$, so that the following applies to the overall heat rate, i.e., the time derivation of the temperature:

$$\frac{dT}{dt} = \beta_u + u_t(t) \quad (14)$$

An important class of these procedures is characterized in that the response signal corresponds to a heat flow of a dynamic thermal analytical method. This heat flow includes, for the excitation signal specified above, a reversible linear portion y(t), which follows the variable portion u(t) of the heat rate, and a non-reversible portion, which may be described, for example, as a time-linear function, resulting overall in the following representation:

$$\frac{dQ}{dt} = \alpha_0 + \alpha_1 t + y(t) \quad (15)$$

In this case, the equation system discussed above takes on the following form:

$$y_k = \gamma_1 + \gamma_2 \cdot t_k - a_1 \cdot y_{k-1} - a_2 \cdot y_{k-2} \ldots - a_{na} \cdot y_{k-na} + b_1 \cdot u_{k-1} + \quad (16)$$
$$b_2 \cdot u_{k-2} \ldots + b_{nb} \cdot u_{k-nb}$$

$$\Theta = [\gamma_1 \gamma_2 a_1 a_2 \ldots a_{na} b_1 b_2 \ldots b_{nb}]^t$$

$$\alpha_1 = \frac{\gamma_2}{1 + \sum_{i=1}^{na} a_i} \quad \alpha_0 = \frac{\gamma_1 + \alpha_1 \cdot \left(\sum_{i=1}^{na} i \cdot a_i\right)}{1 + \sum_{i=1}^{na} a_i}$$

wherein the parameters $a_1, a_2, \ldots, a_{na}, b_1, b_2, \ldots, b_{nb}$ determine the reversible portion described by the time-invariant linear model and the parameters $\gamma_1, \gamma_2$ determine the non-reversible portion. With the thus-determined parameters $a_1, a_2, \ldots, a_{na}, b_1, b_2, \ldots, b_{nb}$, the z transformed value H(z) of the transfer function is determined in accordance with equation (12).

For the argument z, values in the form of $$z = e^{j\omega} \quad (17)$$

are substituted. For these values, the z transformed transfer function H(z) is a function of the frequency w, which can be expressed in the form of $$H(z) = H(e^{j\omega}) = G(j\omega) = Re\,G(j\omega) + Im\,G(j\omega) \quad (18)$$

The value of the function G for the frequency ω=0 yields the thermal capacity of the substance in accordance with $$c_p = \frac{1}{m} G(0) \quad (19)$$

wherein m is the mass of the substance sample to be analyzed. The value of the function G $$|G(j\omega)| = \sqrt{[ReG(j\omega)]^2 + [ImG(j\omega)]^2} \quad (20)$$

and its phase angle $$\mathrm{phase}G(j\omega) = \arctan\frac{\mathrm{Im}G(j\omega)}{\mathrm{Re}G(j\omega)} \quad (21)$$

results in the frequency-dependent complex thermal capacity $c^*_p$ in accordance with $$c_p^* = \frac{1}{m}|G(j\omega)| \qquad (22)$$

as well as the real and imaginary portion in accordance with $$c_p' = c_p^* \cos(\text{phase})$$

$$c_p'' = c_p^* \sin(\text{phase}) \qquad (23)$$

Thus, the determination of the parameters of the model and hence the transfer function makes it possible to evaluate the characteristic quantities of the substance for various frequencies ω.

Heat flows can be measured by capturing a temperature difference which occurs lengthwise along the heat flow path. In addition to the heat flow portion produced by the substance to be analyzed, however, the heat flows include other portions produced by the calorimetric system used to carry out the thermal analysis procedure. In this case, the evaluation based on methods in accordance with the present invention yields the entire heat flow, including its system-induced portions.

However, the evaluation in accordance with the present invention can also be applied to such methods where the heat flow is a difference of heat flows to a sample of the substance and a known reference substance. In these difference procedures, the system-inherent portion is smaller.

Methods in accordance with the present invention can also be applied advantageously in the case where the sample corresponds to an inert reference sample or in which the system is excited without sample. In this case, the process yields the equipment properties.

Furthermore, methods in accordance with the present invention can be applied, advantageously, in the case where the response signal corresponds to a temperature difference of a known dynamic thermal analytical method.

Evaluation methods in accordance with the present invention can also be applied, advantageously, in the case where the response signal corresponds to a thermal output difference of a dynamic output compensation thermal-analytical method. In output compensation methods, the sample of the substance to be analyzed and a known reference substance with varying heat output are excited such that the temperature difference between samples and reference is always regulated to zero. In this case, the response of the sample to be evaluated consists of the different power consumption in comparison to the reference.

Furthermore, methods in accordance with the present invention can be applied advantageously in the case where the response signal corresponds to a change in length of a dynamic thermo-mechanical analytical method. Under the influence of the temperature program corresponding to the excitation signal, a sample capable of shrinking can show, simultaneously, a thermal expansion and a shrinkage overlapping it. Evaluation methods in accordance with the present invention allows the simultaneous determination of the expansion behavior as a reversible portion and the shrinkage behavior as a non-reversible portion.

In general, it should also be pointed out that the excitation may be known from the outset so that its values do not have to be measured. But this is not a necessary requirement for the present invention. Instead, the excitation may be unknown and its values may be determined by measurement. In this case, devices suitable for the implementation of methods in accordance with the present invention are equipped with a measuring device designed to measure the values of the excitation.

In the following description, the present invention is explained in more detail in reference to the drawings.

According to the vertical section illustrated in FIG. 1, a difference calorimeter comprises a hollow cylindrical oven block 1 made of silver, the oven block being capable of being heated by a flat resistance heating element 2. The oven block 1 is sealed, at its top, by a lid arrangement 3, which can be removed in order to provide access to the interior 4 of the oven block 1 for purposes of loading. A disk-shaped substrate 5, which is thermally coupled to the oven block 1, extends into the interior 4 of the oven block 1.

On the horizontally extending upper radial plane of the disk-shaped substrate 5, there is a position for receiving a sample pan 6 and a position for receiving a reference pan 7 in a thermally symmetric arrangement. The positions of the sample pan 6 and the reference pan 7 are provided with one thermal element arrangement each. In the embodiment illustrated, two electrically opposite ends of the two thermal element arrangements on the substrate 5 are interconnected, while the other two ends exit the oven block 1 in the signal lines 8, of which only two are schematically illustrated. This has the result that a thermoelectric signal, which corresponds to the temperature difference ΔT between the sample position and the reference position, occurs in the two lines 8. This thermoelectric signal corresponds, in a known manner, to the difference of the two heat flows which flow between the oven block 1 and the sample pan 6, on the one hand, and the oven block 1 and the reference pan 7, on the other hand.

The resistance heating element 2 is connected—in a manner not illustrated—to a controlled power source which supplies electrical heat energy. The control is effected such that a preset dynamic temperature sequence is cycled through as a function of time. This temperature sequence is captured with a platinum thermometer 9, arranged in the oven block 1, whose output signal exits the oven block 1 on a schematically illustrated signal line 10. Thus, the signal lines 10 carry a signal which corresponds to the preset temperature sequence.

The reference numbers 11, 12, and 13 designate a flushing gas inlet line, a flushing gas outlet line or a dry gas feed line. Furthermore, the reference numbers 14, 15 and 16 designate, in a generally known manner, a cooling flange, a cooling finger or a platinum thermometer. A thermal resistance 17 is arranged between the cooling arrangement 14, 15 and the resistance heating element 2.

In this difference calorimeter, the temperature sequence to which a sample in the sample pan 6 inside the oven block 1 is exposed serves as excitation. The signal in the signal line 10, with said signal representing the temperature sequence, is sampled by an analysis unit, using a sufficiently large sampling rate, and differentiated by time, which allows one to obtain the time derivation of the temperature sequence, i.e. the heat rate. Synchronously, the temperature difference signal ΔT occurring on the signal line 8 is also sampled, with the temperature difference signal ΔT representing the difference heat flow as a response to the excitation.

Figure 2:
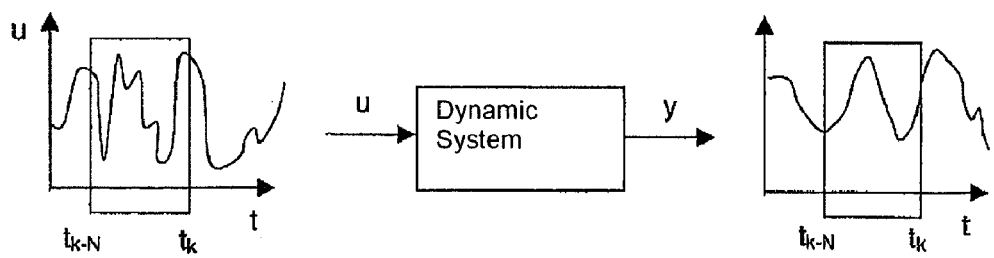
FIG. 2 is a schematic illustrating an evaluation process in an embodiment of the method in accordance with the present invention.

In this way, one obtains a time series of measurement points of the excitation signal $u(t_k)$, $u(t_{k-1})$, ..., provided by the heat rate, as well as the response signal $y(t_k)$, $y(t_{k-1})$, .... This is schematically illustrated in FIG. 2. In FIG. 2, the series of measurement values framed between $t_k$ and $t_{k-N}$ designates an evaluation window with a number of measurement points sufficient for the solution of the equation system (4) or (16), which were discussed above. This means that $N \geq (n_a + n_b)$. The parameter values of the model are thus newly determined for every position of the evaluation window within the entire measured temperature sequence. Using the thus-determined parameters, the z transform of the transfer function may be determined in accordance with equation (12).

Figure 3:
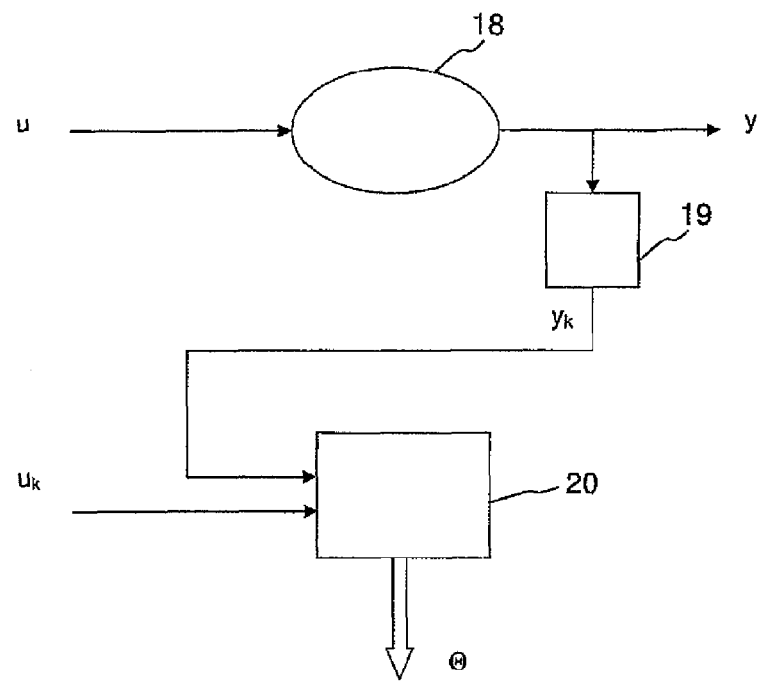
FIG. 3 is a diagram of illustrating an evaluation process for the determination of model parameters in accordance with the present invention.

This is illustrated in more detail in FIG. 3, where u designates the excitation signal and y designates the response signal. The value of the excitation signal $u(t_k)$—which is either known from the outset or determined by measurement—at the sampling time $t_k$ is designated as $u_k$. In a similar manner, $y_k$ designates the measured value of the response signal $y(t_k)$ at the sampling time $t_k$. The vector of the parameter values, specified above in equation (3), is designated as $\Theta$.

With these designations, FIG. 3 illustrates the effect of the excitation u on the substance sample 18 and the associated response emitted by the substance sample 18. A measurement device 19 samples the response y and delivers the sampling values $y_k$ to an evaluation device 20. The values $u_k$ of the excitation, assumed as known in FIG. 3, are also fed to this evaluation device 20. Based on these input values, the evaluation device determines the vector $\Theta$ of the parameter values in the manner illustrated above using equations (1) to (16).

Figure 4:
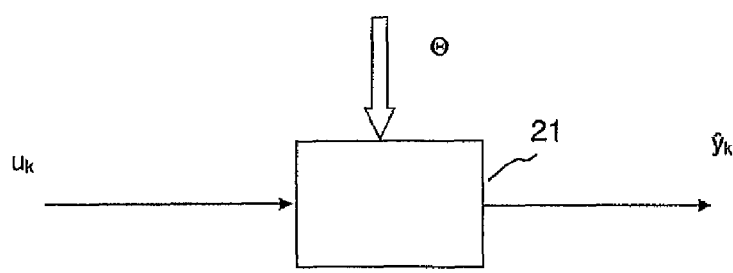
FIG. 4 is a diagram illustrating a calculation of response values by a model in accordance with the present invention.

FIG. 4 symbolizes the substitution of the vector $\Theta$ of the parameter values, obtained as illustrated in FIG. 3, in the mathematical model 21. The latter thus models the correlation between the excitation and the response. As illustrated in FIG. 4, this would also allow the calculation of estimates $\hat{y}_k$ of the response, corresponding to any values $u_k$ of the excitation.

In the example illustrated above, the response signal represents the heat flow difference between the sample and the reference. In the thermo-mechanical analysis, on the other hand, the change in length of a sample exposed to a temperature sequence is captured as the response signal.

The analysis explained above is suitable for virtually all signal forms of the dynamic excitation signal u(t). Specifically, the excitation signal may be a stochastic signal or a pseudo stochastic signal, in which a stochastic signal sequence of finite duration is repeated.

The invention claimed is:

1. A method for analyzing a substance, wherein the method is executed by a device configured to analyze a substance, the method comprising:
   subjecting, by the device, the substance to a dynamic excitation to produce an observable response; and
   determining, by the device, a characteristic quantity of the substance based on a correlation between the excitation and the response, wherein the correlation between the excitation and the response is expressed by a parametric model for which a specific model structure with a finite number of unspecified parameters is preset, the determining including:
      calculating, by the device, the parameters of the model from values of the excitation and the response in a time domain;
      determining, by the device, from the calculated parameters a transfer function in a frequency range; and
      calculating, by the device, the characteristic quantity directly from the transfer function.

2. The method of claim 1, wherein the transfer function is calculated for at least one frequency as the characteristic quantity.

3. The method of claim 2, wherein the transfer function for a zero frequency is calculated as the characteristic quantity.

4. The method of claim 1, wherein a phase angle of the transfer function for at least one frequency is calculated as the characteristic quantity.

5. The method of claim 1, wherein the parameters of the model are calculated from values of the excitation and the response for a time series of values, and wherein a z transform of the transfer function is calculated from the parameters and used as the transfer function in the frequency range for purely imaginary values of z.

6. The method of claim 5, wherein the correlation between the excitation and the response is represented as a difference equation, wherein a number $n_b$ of values $u_{k-1}, \ldots, U_{k-nb}$ of the excitation, having an equal time interval, and a number $n_a$ of values $y_{k-1}, \ldots, y_{k-na}$, of the response are multiplied by a respective number of coefficients $a_1, \ldots, a_{na}$, and wherein the coefficients $a_1, \ldots, a_{na}, b_1, \ldots, b_{nb}$ represent the model parameters.

7. The method of claim 6, wherein a sufficient time series of values of excitation and the response are substituted in the difference equation for its resolution based on the coefficients.

8. The method of claim 7, wherein an equation error occurring in the resolution is minimized.

9. The method of claim 5, wherein the parameters are set as constant in terms of time for a time interval including at least the time series of the values of the excitation.

10. The method of claim 5, wherein for different time intervals, the parameters are determined separately by means of time series selected within each time interval.

11. The method of claim 1, wherein the model is set as time-invariant and linear.

12. The method of claim 11, wherein a mathematical term is added to the time-invariant, linear portion, with said mathematical term serving to take into account a non-linear portion in the response.

13. The method of claim 1, wherein the substance analysis is a thermal analytical method.

14. The method of claim 13, wherein the response comprises a response quantity corresponding to a temperature difference of a dynamic thermal analytical method.

15. The method of claim 13, wherein the response includes a response quantity which corresponds to a heat flow of a dynamic thermal analytical method.

16. The method of claim 15, wherein the heat flow is a difference of heat flows to a sample of the substance and a known reference substance.

17. The method of claim 13, wherein the response includes a response quantity which corresponds to a thermal output difference of a dynamic output compensation thermal analytical method.

18. The method of claim 13, wherein the response includes a response quantity which corresponds to a change of length of a dynamic thermo-mechanical analytical method.

19. The method of claim 13, wherein the response includes a response quantity which corresponds to a weight change of a dynamic thermo-gravimetric analytical method.

20. The method of claim 1, wherein the excitation includes an excitation quantity which corresponds to a variable temperature.

21. The method of claim 1, wherein the excitation includes an excitation quantity which corresponds to a variable output.

22. The method of claim 1, wherein the excitation includes an excitation quantity which corresponds to a variable pressure.

23. The method of claim 1, wherein the excitation includes an excitation quantity which corresponds to a variable radiation.

24. The method of claim 1, wherein the excitation includes an excitation quantity which corresponds to a variable tension or expansion.

25. The method of claim 1, wherein the excitation includes an excitation quantity which corresponds to a variable gas atmosphere.

26. The method of claim 1, wherein the excitation includes an excitation quantity which corresponds to a variable magnetic field.

27. The method of claim 1, wherein the response includes a response quantity which corresponds to a force of a dynamic mechanical analytical method.

28. The method of claim 1, wherein the response includes a response quantity which corresponds to a change in length of a dynamic mechanical analytical method.

29. The method of claim 1, wherein the response includes a response quantity which corresponds to a tension change of a dynamic mechanical analytical method.

30. The method of claim 1, wherein the substance is subjected to the dynamic excitation in a device, and wherein the method further comprises:
performing the dynamic excitation without the substance therein to produce another observable response; and
determining a characteristic quantity of the device based on a correlation between the excitation and the response produced without the substance therein.

31. A device for analyzing a substance, comprising:
excitation means by which a sample of the substance is exposed to a dynamic excitation to produce an observable response;
a measurement device for measuring the response; and
an evaluation device for determining a characteristic quantity of the substance based on a correlation between the excitation and the response from the measurement device, wherein the evaluation device comprises a computing mechanism configured to:
calculate parameters for a parametric model describing the correlation between the excitation and the response, the parametric model having a specific model structure and a finite number of unspecified parameters, wherein the parameters are calculated from the values of the excitation and the response in a time domain;
determine from the calculated parameters a transfer function in a frequency range; and
calculate the characteristic quantity directly from the transfer function.

32. The device of claim 31, wherein the excitation means includes means for producing a temperature sequence as a function of time and thermal coupling means for thermally coupling the sample with the measurement device for measuring a heat flow influenced by the sample.

33. The device of claim 32, wherein the thermal coupling means includes means for symmetrically thermally coupling a reference material with the measurement device, and wherein the measurement device is configured to measure the difference between the heat flow to the sample and the heat flow to the reference material.

34. The device of claim 31, wherein the excitation means includes:
means for producing a temperature sequence as a function of time;
means for thermally coupling the sample with a reference material; and
means for regulating a temperature difference between the sample and the reference material to zero;
wherein the measurement device is configured to measure the difference between a heat output fed to the sample and the heat output fed to the reference material, the heat output difference being necessary for the zero regulation of the temperature difference.

35. The device of claim 31, wherein the excitation means includes means for producing a temperature sequence as a function of time, and further including thermal coupling means for thermally coupling the sample with the measurement device to measure a change in length of the sample.

36. The device of claim 31, further comprising a device for producing the values of the excitation signal to measure an excitation signal corresponding to the excitation.

* * * * *